(12) United States Patent
Yu

(10) Patent No.: US 10,786,213 B2
(45) Date of Patent: Sep. 29, 2020

(54) CT MACHINE AND ROTATOR THEREOF

(71) Applicant: Beijing Neusoft Medical Equipment Co., Ltd., Beijing (CN)

(72) Inventor: Jun Yu, Shenyang (CN)

(73) Assignee: BEIJING NEUSOFT MEDICAL EQUIPMENT CO., LTD., Beijing (CN)

(*) Notice: Subject to any disclaimer, the term of this patent is extended or adjusted under 35 U.S.C. 154(b) by 194 days.

(21) Appl. No.: 15/793,928

(22) Filed: Oct. 25, 2017

(65) Prior Publication Data

US 2018/0110481 A1   Apr. 26, 2018

(30) Foreign Application Priority Data

Oct. 26, 2016 (CN) ........................ 2016 1 0950664

(51) Int. Cl.
*A61B 6/03* (2006.01)
*A61B 6/08* (2006.01)
*A61B 6/00* (2006.01)

(52) U.S. Cl.
CPC ............. *A61B 6/035* (2013.01); *A61B 6/08* (2013.01); *A61B 6/44* (2013.01)

(58) Field of Classification Search
CPC ...... A61B 6/032; A61B 6/035; G01N 23/046; G01N 2223/419; G06T 2211/40; G06T 2207/10081
See application file for complete search history.

(56) References Cited

U.S. PATENT DOCUMENTS

| 6,819,737 | B2* | 11/2004 | Suzuki | ............... | A61B 6/035 378/15 |
| 2007/0053479 | A1* | 3/2007 | Sadatomo | ........... | A61B 6/035 378/4 |
| 2008/0197303 | A1* | 8/2008 | Aoi | ..................... | A61N 5/10 250/522.1 |
| 2010/0025591 | A1 | 2/2010 | Luecke et al. | | |
| 2017/0325764 | A1* | 11/2017 | Yun | ................... | A61B 6/035 |

FOREIGN PATENT DOCUMENTS

| CN | 1927121 A | 3/2007 |
| CN | 203524687 U | 4/2014 |
| CN | 104735891 A | 6/2015 |
| JP | 2003070777 A | 3/2003 |
| JP | 2005118070 A | 5/2005 |
| KR | 101254098 B1 | 4/2013 |

OTHER PUBLICATIONS

State Intellectual Property Office of the People's Republic of China, Office Action and Search Report Issued in Application No. 201610950664.3, dated Jun. 29, 2020, 15 pages. (Submitted with Machine Translation).

* cited by examiner

*Primary Examiner* — David P Porta
*Assistant Examiner* — Mamadou Faye
(74) *Attorney, Agent, or Firm* — McCoy Russell LLP

(57) ABSTRACT

A Computed Tomography (CT) machine and a rotator thereof are provided. The rotator includes a rotating base with a scanning hole, a reinforcement with an axial through hole, and a load-carrying part for carrying scanning parts. The reinforcement is of a circumferentially closed structure. The axial through hole communicates with the scanning hole in a way that the reinforcement does not axially block the scanning hole. The load-carrying part is mounted on an external peripheral surface of the rotating base, and an axial end of the load-carrying part is connected with the reinforcement.

20 Claims, 5 Drawing Sheets

CT MACHINE AND ROTATOR THEREOF

CROSS REFERENCE TO RELATED APPLICATIONS

This application claims priority to Chinese Patent Application No. 201610950664.3, filed on Oct. 26, 2016, the entire contents of which are incorporated herein by reference for all purposes.

TECHNICAL FIELD

The present disclosure relates to a CT machine and a rotator thereof.

BACKGROUND

A CT (Computed Tomography) machine may include a scanning bed system and a scanning gantry system. The scanning bed system may be used to carry a subject. The scanning gantry system may include a rotating system and may be rotated around the subject. The rotating system may include scanning parts and a rotator. The scanning parts may include a tube, a high voltage generator, a detector and so on. The scanning parts may be carried by the rotator.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

Figure 1:
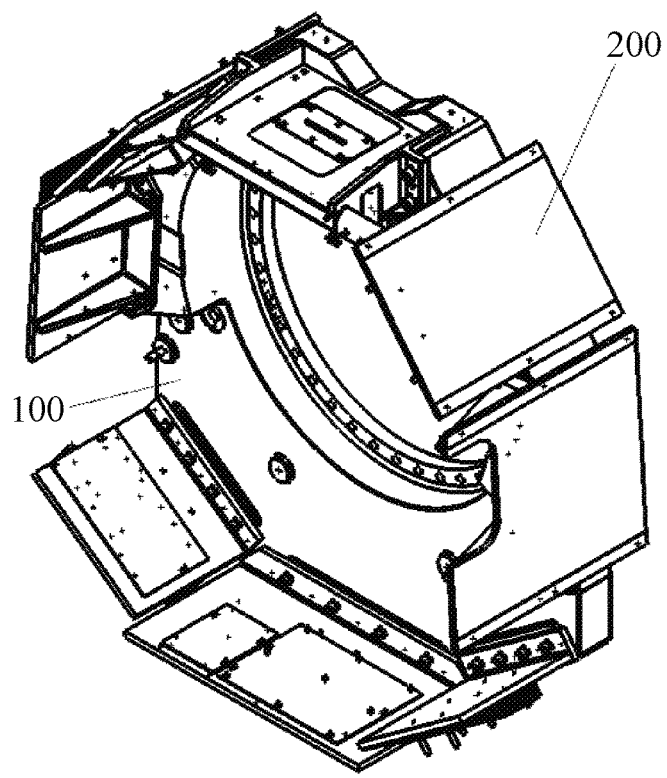
FIG. 1 is a schematic structure diagram of a rotator according to an example of the present disclosure.
Figure 2:
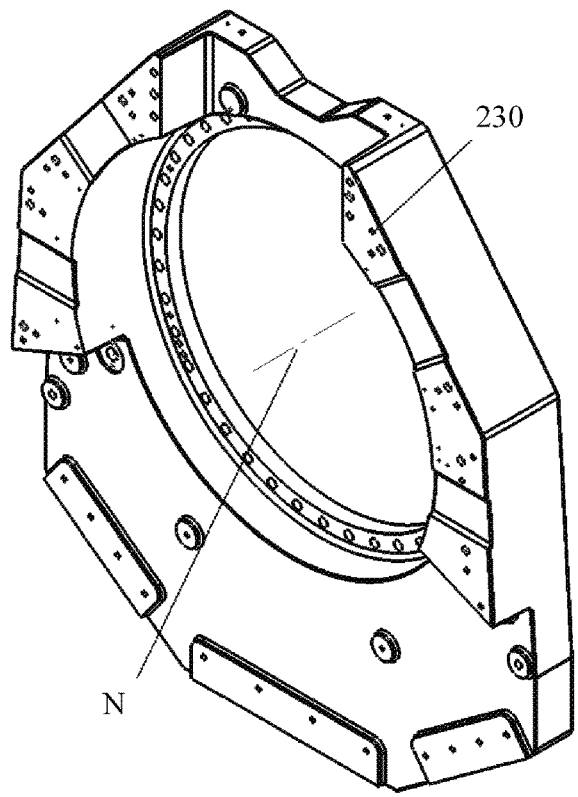
FIG. 2 is a schematic structure diagram of a casting base in the rotator shown in FIG. 1.
Figure 3:
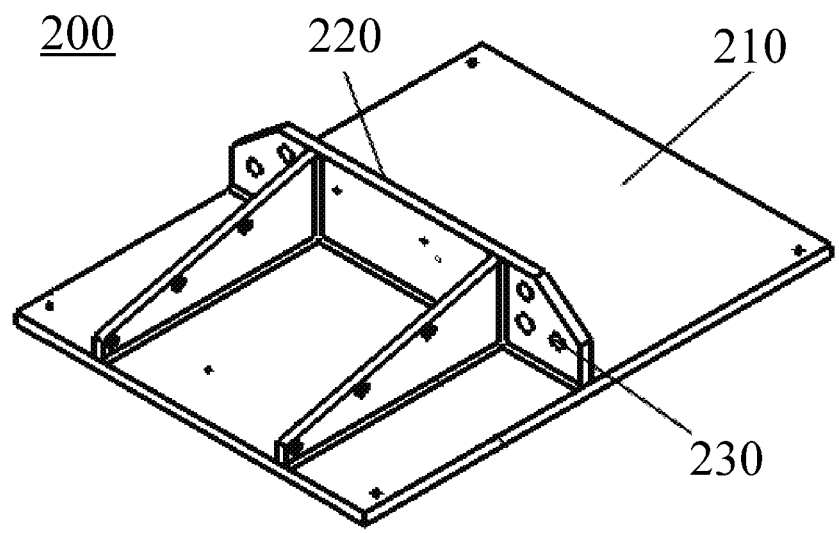
FIG. 3 is a schematic structure diagram of a support frame in the rotator shown in FIG. 1.
Figure 4:
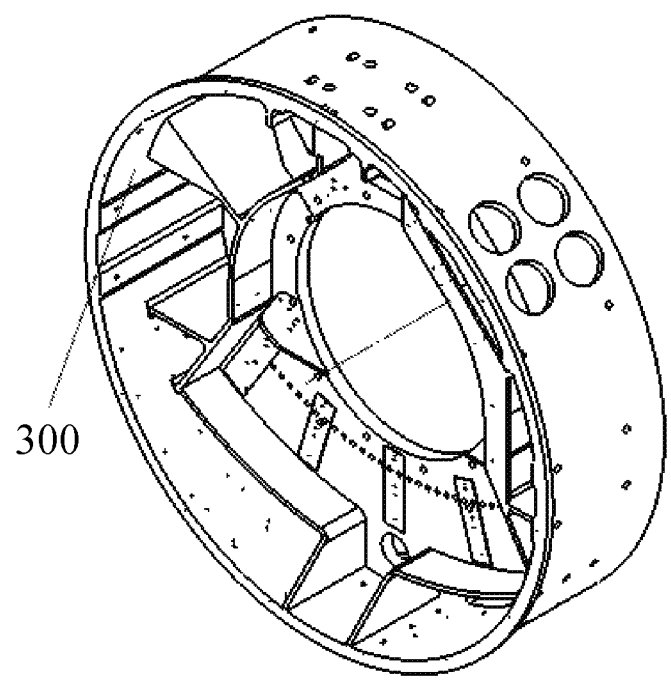
FIG. 4 is a schematic structure diagram of a rotator according to another example of the present disclosure.

Referring to FIG. 1 to FIG. 4, FIG. 1 is a schematic structure diagram of a rotator according to an example of the present disclosure; FIG. 2 is a schematic structure diagram of a casting base in the rotator shown in FIG. 1; FIG. 3 is a schematic structure diagram of a support frame in the rotator shown in FIG. 1; and FIG. 4 is a schematic structure diagram of a rotator according to another example of the present disclosure.

As shown in FIG. 1, a structure of a rotator on a CT machine may be of a support combination type. The rotator may include a casting base 100 and a plurality of support frames 200. In the rotator, a supporting plane for carrying scanning parts such as a tube, a high voltage generator, a detector and so on may be provided on an external side surface of the rotator. As shown in FIG. 2, an axis of respective holes for fixing the support frame 200 in the casting base 100 may be parallel to a rotating axis N of the rotator. The structure of the support frame 200 may include a ribbed T-shaped structure as shown in FIG. 3. A transverse portion of the T-shaped structure may form a flat plate 210 and a vertical portion of the T-shaped structure may form a vertical plate 220. Fixing holes in the flat plate 210 may be used to fix scanning parts such as a high voltage generator, a tube and so on. Support frame fixing holes 230 provided in the vertical plate 220 may be used to connect the casting base 100 and thus fix the support frame 200.

In an example, the support combination type rotator shown in FIG. 1 may be manufactured by welding to achieve the T-shaped structure of the support frame 200. However, during a long-term rotation process, fatigue degradation may happen to some weld joints due to welding operations. For example, the fatigue degradation may include scanning parts dislodging from the rotator.

In addition, the vertical plate 220 of the support frame 200 may be pressed tightly with axial forces of screws fixed in the support frame fixing holes 230, so that the vertical plate 220 can fit the casting base 100. Thus, a centrifugal force generated from a rotation may be resisted by a frictional force between the vertical plate 220 and the casting base 100 to maintain the position of the support frame 200 unchanged. In an example, the axial forces of screws are multiplied by a friction coefficient to obtain the frictional force. The friction coefficient typically ranges from 0.1 to 0.25. In other words, if an axial force of one screw is transformed into a frictional force, 90% of the axial force of the screw may be lost. In this case, to avoid the degradation described above, bigger or more screws or pins may be used to fix the support frame 200, thereby resulting in complex structure and high manufacturing cost.

Further, a rotating speed of the CT machine may be 0.2 second per rotation to 0.5 second per rotation. The fixed scanning parts may bear different centrifugal forces because distances from the rotating axis N are different. In an example, a centrifugal acceleration of a scanning part bearing the maximum centrifugal force may reach 80 g or more (e.g., a centrifugal force generated by 1 Kg of a load after rotation is equivalent to a weight of 80 Kg), and thus the stiffness of the casting base 100 and the flat plate 210 is desired to be more.

In an example, a focal spot of the tube and an axial symmetrical center line of a detector may form an X-ray plane. If the rotator is deformed during a rotation process, it may cause distortion of an X-ray path, thereby affecting the accuracy of collected data. In addition, the T-shaped support frame 200 is of a cantilever structure, which may be susceptible to degradation under the centrifugal force generated from high speed rotation.

In another example, as shown in FIG. 4, the rotator for the CT machine may be a cylindrical rotator, and a supporting plane 300 for carrying scanning parts such as a tube, a high voltage generator and so on may be provided inside an outer ring of the rotator. The rotator may be integrally formed with aluminum alloy through casting.

For the cylindrical rotator, since a load-carrying structure for fixing each of the scanning parts may be located at the outer ring of the cylindrical rotator, the outer ring of the cylindrical rotator shall be relatively heavy. The load-carrying structure may have a relatively large rotating radius corresponding to a center of gravity for the load-carrying structure. The rotating system constituted by the rotator with such a structure may have a relatively greater rotary inertia, which may restrict a rotational scanning speed of the CT machine.

The present disclosure provides a CT machine and a rotator thereof, which can resist deformation of the rotator, improve integral stiffness of the rotator and satisfy the demand of high speed rotational scanning, simplify the structure of the rotator, and reduce the weight of the rotator.

Figure 5:
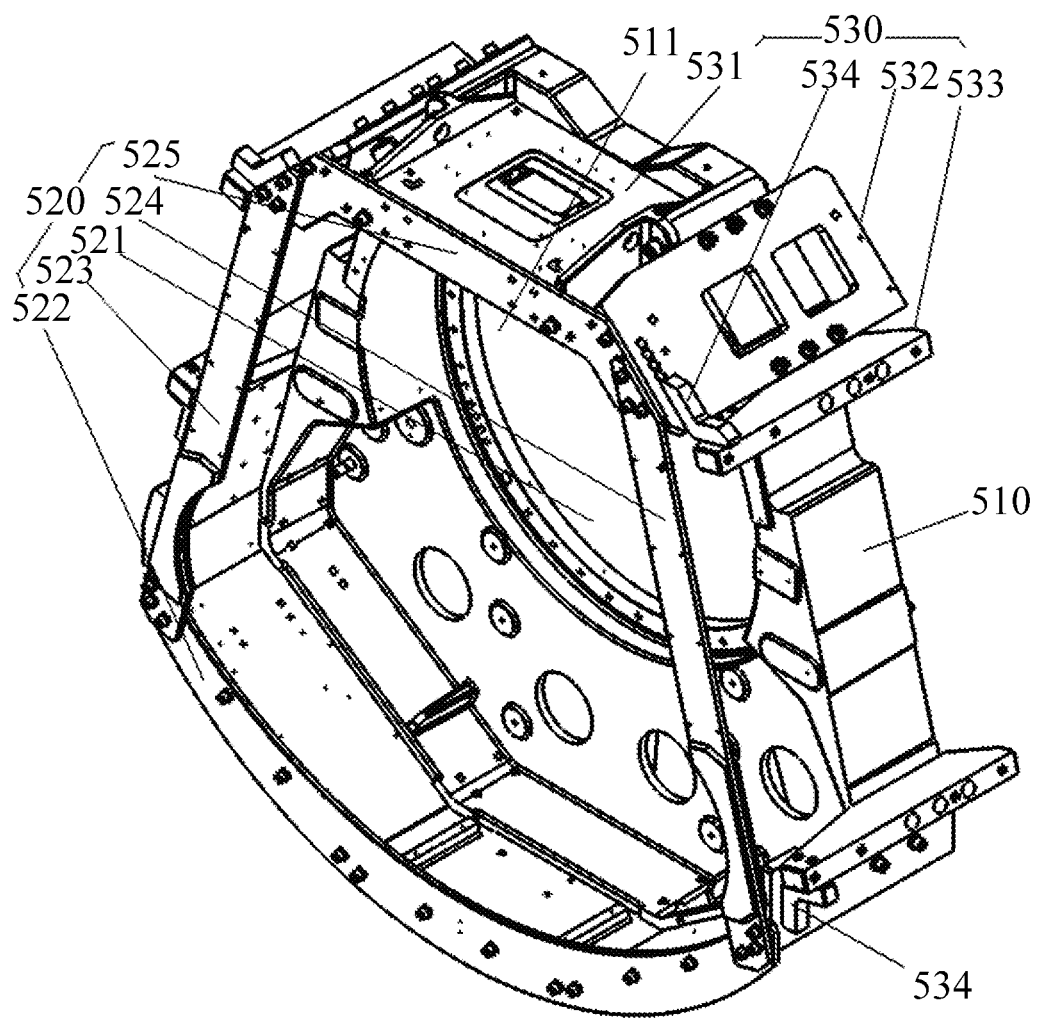
FIG. 5 is a schematic structure diagram of a rotator of a CT machine according to one or more examples of the present disclosure.

FIG. 5 illustrates a schematic structure diagram of a rotator of a CT machine according to one or more examples of the present disclosure. As shown in FIG. 5, the rotator may include a rotating base 510, a load-carrying part 530 and a reinforcement 520. The rotating base 510 may have a scanning hole 511 to accommodate a scanned portion of a subject. The load-carrying part 530 may be used to carry scanning parts, such as a tube, a detector, a high voltage generator and so on for scanning. The load-carrying part 530 may be mounted on an external peripheral surface of the rotating base 510, and the external peripheral surface of the load-carrying part 530 may form a mounting plane for the scanning parts. Thus, the scanning parts may be fixed by the load-carrying part 530, and the load-carrying part 530 may be connected with the rotating base 510. The reinforcement 520 may be connected with an axial end of the load-carrying part 530 to reinforce the load-carrying part 530. Since the load-carrying part 530 is distributed at the external peripheral surface of the rotating base 510, when high speed rotational scanning is performed, the load-carrying part 530 and the scanning parts carried thereon may bear a relatively great centrifugal force. In this way, the rotator may be relatively easily deformed, such as at an X-ray plane. However, since the reinforcement 520 is of a circumferentially closed structure, a constraining force for resisting the centrifugal force may be provided for the load-carrying part 530, thereby effectively suppressing deformation of the rotator at the X-ray plane and improving integral stiffness of the rotator.

The X-ray plane refers to a plane formed by a focal spot of the tube emitting an X-ray beam and an axial symmetric center line of a detector receiving the X-ray beam. If the rotator is deformed during a rotation process, the relative positions of the tube and the detector may be changed, which will cause distortion of an X-ray path, thereby affecting the accuracy of collected data.

The rotator in the present disclosure is provided with the reinforcement 520. Scanning parts are carried by the load-carrying part 530. The load-carrying part 530 is mounted on the external peripheral surface of the rotating base 510. The axial end of the load-carrying part 530 is connected with the reinforcement 520. Since the reinforcement 520 is of the circumferentially closed structure, it may provide the constraining force for the load-carrying part 530. For example, the reinforcement 520 may provide the constraining force pointing to a scanning center from outside to inside in the X-ray plane for the load-carrying part 530, so as to resist the centrifugal force generated from the high speed rotational scanning process and suppress the deformation of the rotator in the X-ray plane, thereby ensuring the accuracy of the collected data.

Moreover, the reinforcement 520 may facilitate positioning of the axial end of the load-carrying part 530 and then may improve the stiffness and positioning reliability of the load-carrying part 530, thereby ensuring that the scanning parts carried by the load-carrying part 530 are mounted and fixed accurately and reliably.

Furthermore, the reinforcement 520 further includes an axial through hole 521 which communicates with the scanning hole 511 of the rotating base 510. In this way, it may be avoided that the scanning operation is affected in a case that the scanning hole 511 is blocked by the reinforcement 520. Here, the axial through hole 521 of the reinforcement 520 may be disposed coaxially with the scanning hole 511. In an example, the axial through hole 521 and the scanning hole 511 may have equal diameters. In another example, the diameter of the axial through hole 521 may be slightly greater than that of the scanning hole 511. Since the reinforcement 520 is connected with the axial end of the load-carrying part 530 and the load-carrying part 530 is mounted on the external peripheral surface of the rotating base 510, the reinforcement 520 may be located at an axial end of the rotating base 510.

Figure 6:
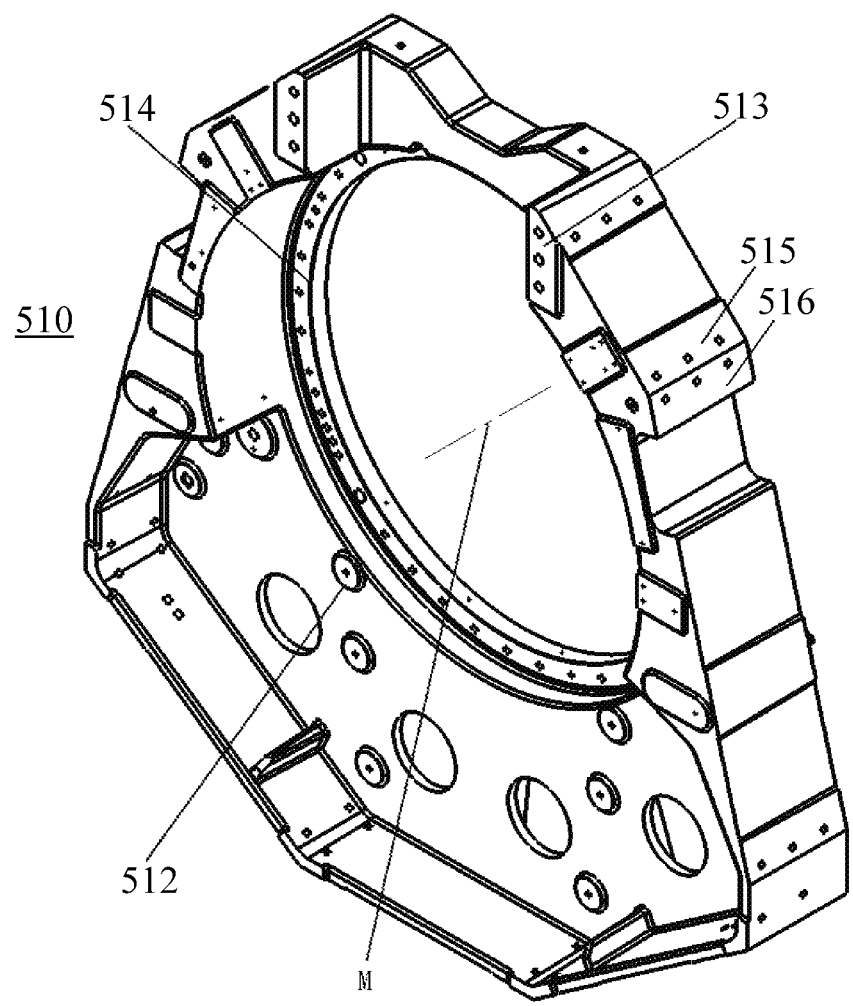
FIG. 6 is a schematic structure diagram of a rotating base in the rotator shown in FIG. 5.

With reference to a central axis of the scanning hole 511, e.g., a rotating axis M, a direction near the rotating axis M is inside and a direction away from the rotating axis M is outside. An internal peripheral surface of the rotating base 510 defines the scanning hole 511. A portion located at an outer edge of the rotating base 510 forms the external peripheral surface thereof. The external peripheral surface herein is relative to the internal peripheral surface. Although the scanning hole 511 is a round hole, the rotating base 510 is not limited to a strictly circular ring type structure. In other words, the external peripheral surface of the rotating base 510 is not necessarily in a strictly circumferential shape as long as it can be circumferentially enclosed. For example, as shown in FIG. 6, the external periphery surface of the rotating base 510 may also be in an irregular geometrical shape.

Up and down, left and right, and front and back herein are defined with reference to the normal operating condition of the CT machine. During being operated, a direction perpendicular to the ground is an up-and-down direction. A direction in which the scanning hole 511 faces a scanning bed is front, and a direction in which the scanning hole 511 departs from the scanning bed is back. If a subject lies on the scanning bed with the head at the front and the feet at the back, a direction represented by the left hand is left and a direction represented by the right hand side is right.

The scanning parts may include a tube emitting an X-ray beam, a detector receiving the X-ray beam, and other electrical parts. The connections between different scanning parts can be achieved by the rotator, and thus normal scanning operation may be finished.

To avoid occupying a scanning space by the reinforcement 520 while increasing the constraining force, the reinforcement 520 may be disposed at an axial end of the scanning hole 511, such as, in front of the rotating base 510 and at a relatively inner position outside the scanning hole 511. In an example, an annular region may be formed by an outer edge of the scanning hole 511 radially and outwardly extended for a predetermined distance. The predetermined distance is relatively small, and the annular region is located at a relatively inner position of the rotating base 510. The reinforcement 520 may be disposed at a position corresponding to the annular region and in front of the rotating base 510, so as to effectively constrain the load-carrying part 530.

The reinforcement 520 may be of an integral structure and may also be of a split structure. In an example, as shown in FIG. 5, the reinforcement 520 may include a plurality of pulling plates, and different pulling plates may be circumferentially connected in sequence to form a circumferentially closed structure. For example, the reinforcement 520 may be of a circumferentially closed-loop structure without any gap. In this way, due to the circumferentially closed structure, the pulling plates in the reinforcement 520 may depend on each other circumferentially and the constraining force pointing to the scanning center from outside to inside may be generated, thereby helping the load-carrying part 530 to resist the centrifugal force.

When the reinforcement 520 is formed by connecting the plurality of pulling plates, it does not only facilitate assembly and disassembly due to the simple structure but also better match the rotating base 510, without affecting the normal scanning operation. The strength and size of the pulling plate may also be set according to requirements to provide the sufficient constraining force to resist the centrifugal force.

The plurality of pulling plates means that the number of the pulling plates is uncertain. For example, there may be more than three pulling plates.

As shown in FIG. 5, the reinforcement 520 may include a first pulling plate 522, and the first pulling plate 522 may be an arc-shaped plate capable of matching the detector among the scanning parts. Correspondingly, the rotating base 510 includes a detector mounting plane 512 as shown in FIG. 6, and the first pulling plate 522 may be approximately located at a front axial end of the detector mounting plane 512 and set approximately perpendicular to the detector mounting plane 512. In this case, the detector mounting plane 512 and the first pulling plate 522 may together form a cavity for mounting the detector.

The reinforcement 520 may further include a second pulling plate 523 and a third pulling plate 524 both extended from top to bottom. Respective lower ends of the second pulling plate 523 and the third pulling plate 524 are connected with the two ends of the first pulling plate 522, respectively, and respective upper ends of the second pulling plate 523 and the third pulling plate 524 are connected by a fourth pulling plate 525. In other words, the reinforcement 520 may further include the fourth pulling plate 525. In this case, the reinforcement 520 is approximately of a trapezoid structure, and the axial through hole 521 slightly larger than the scanning hole 511 may be formed in the middle portion of the trapezoid structure, in front of the scanning hole 511.

The second pulling plate 523 and the third pulling plate 524 may obliquely extend from top to bottom, so as to avoid blocking the scanning hole 511. Moreover, as shown in FIG. 5, the second pulling plate 523 and the third pulling plate 524 may be inclined along opposite directions, where the second pulling plate 523 is inclined from bottom to top to the right in FIG. 5 and the third pulling plate 524 is inclined from bottom to top to the left in FIG. 5. Thus, the second pulling plate 523 and the third pulling plate 524 are both inclined in the direction near the scanning hole 511 from bottom to top and are not parallel to one another.

To facilitate mounting the detector, the first pulling plate 522 shall have a particular arc length, for example, have a given size in the left-and-right direction in FIG. 5, and the lower ends of the second pulling plate 523 and the third pulling plate 524 are connected to two ends of the first pulling plate 522, respectively. In this case, the lower ends of the second pulling plate 523 and the third pulling plate 524 are both located at relatively outer positions.

To provide the sufficient constraining force to resist the centrifugal force, the reinforcement 520 may be located at the relatively inner position outside the scanning hole 511. In this case, the upper ends of the second pulling plate 523 and the third pulling plate 524 may be inwardly inclined to connect the first pulling plate 522 and provide the sufficient constraining force to resist the centrifugal force.

The words such as first, second are merely intended to differentiate between two or more parts having the same or similar structures, which are not intended to limit the disposition sequence.

The first pulling plate 522, the second pulling plate 523 and the third pulling plate 524 may all be straight plates, thereby facilitating not only processing and manufacturing, but also connection with the axial end of the load-carrying part 530, improving convenience in assembly and disassembly, contributing to matching the rotating base 510 to provide the sufficient constraining force for the load-carrying part 530.

The reinforcement 520 may also be disposed as a symmetrical structure. For example, the reinforcement 520 may be symmetrical relative to a line connecting the midpoints of the first pulling plate 522 and the fourth pulling plate 525, so that a stable and reliable reinforcing structure can be formed.

In an example, the load-carrying part 530 may further include a ray box (be also referred to as A-plane box) 531 for mounting the tube, and an axial end of the ray box 531 may be connected with the fourth pulling plate 525. In this way, the first pulling plate 522 is located below in FIG. 5, the fourth pulling plate 525 is located above in FIG. 5, and the first pulling plate 522 and the fourth pulling plate 525 are disposed oppositely. Correspondingly, the tube for emitting the X-ray beam and the detector for receiving the X-ray beam are opposite to form a path for transmitting and receiving the X-ray beam.

As shown in FIG. 6, the rotating base 510 further includes a ray box mounting plane 513, a bearing mounting plane 514 and a detector mounting plane 512. The bearing mounting plane 514 may be disposed at an inner ring of the scanning hole 511 of FIG. 5 in a way that the scanning hole 511 is rotated relative to the rotating base 510. A portion beyond the scanning hole 511 in the rotating base 510 may be approximately of an annular structure. The detector mounting plane 512 may be of an arc structure located at a lower portion of the annular structure. Correspondingly, the bearing mounting plane 514 may be an annular ring parallel to the annular structure. The ray box mounting plane 513 may be of a flat plane located at an upper portion of the annular structure, for example, a top surface of the rotating base 510. Thus, the ray box 531 may be of a plate-shaped box structure for mounting the tube. The mounting position of the ray box 531 may be opposite to the mounting position of the detector.

Figure 7:
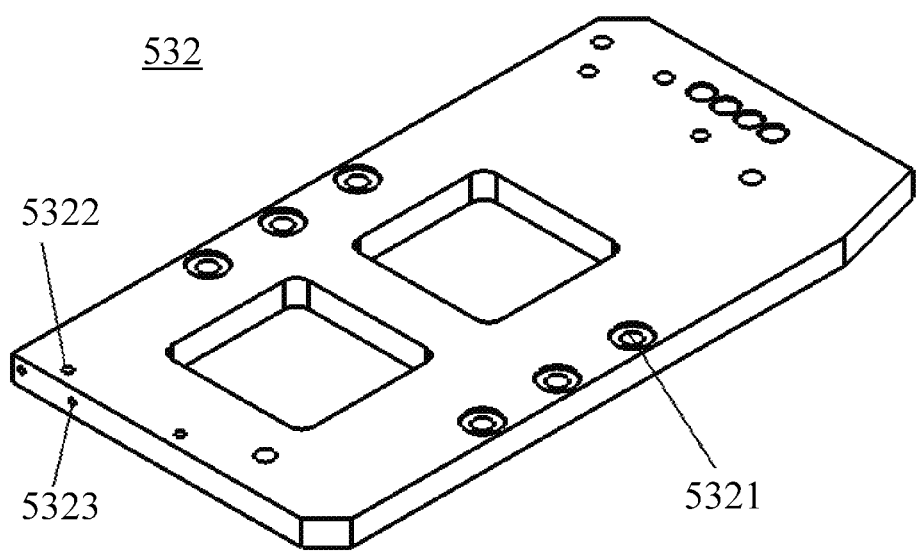
FIG. 7 is a schematic structure diagram of a flat plate type support frame in the rotator shown in FIG. 5.

As shown in FIG. 5 and FIG. 7, the load-carrying part 530 may further include a flat plate type support frame 532. A plate surface of the flat plate type support frame 532 fits the external peripheral surface of the rotating base 510 and is connected with the rotating base 510 by first positioning pieces perpendicular to the rotating axis M. As shown in FIG. 5, in an example, the first positioning pieces may be screws or pins.

The flat plate type support frame 532 may include holes 5321 for mounting the first positioning pieces and holes 5322 for fixing electrical parts. Thus, the flat plate type support frame 532 may be used to mount parts such as a relatively low weight power source, a circuit board and a balance plate.

Figure 8:
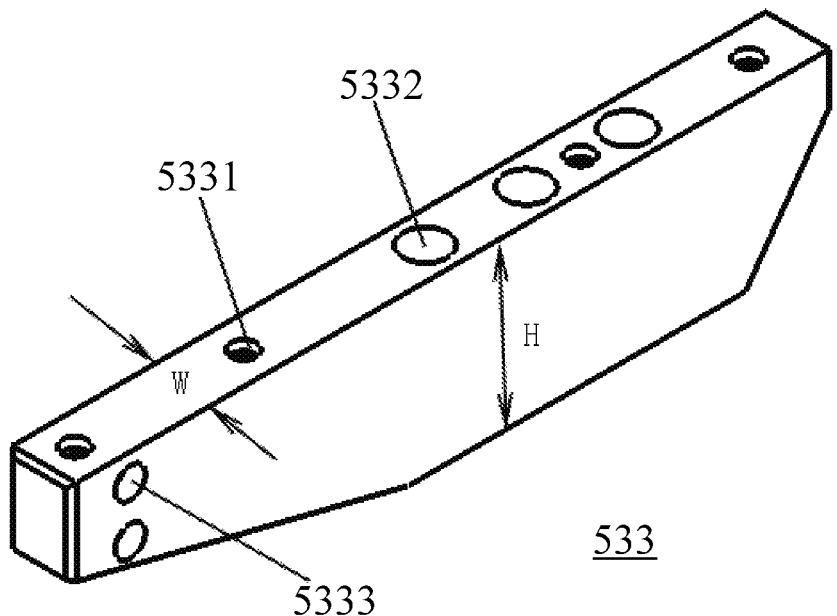
FIG. 8 is a schematic structure diagram of a vertical rib type support frame in the rotator shown in FIG. 5.

As shown in FIG. 5 and FIG. 8, the load-carrying part 530 may further include a vertical rib type support frame 533. The plate surface of the vertical rib type support frame 533 is not parallel to that of the flat plate type support frame 532, for example, the plate surface of the vertical rib type support frame 533 may be approximately perpendicular to that of the flat plate type support frame 532, and connected with the rotating base 510 by second positioning pieces perpendicular to the rotating axis M. Similarly, the second positioning pieces may be screws or pins.

The vertical rib type support frame 533 may include holes 5331 for fixing the second positioning pieces and holes 5332 for fixing the electrical parts. The two types of holes may be located at the same plane, and width W of the plane is far less than height H of the vertical rib type support frame 533. Thus, the vertical rib type support frame 533 may form a high stiffness support frame with a stiffener effect to improve the strength of the whole rotator.

Since the holes 5331 for fixing the second positioning pieces and the holes 5332 for fixing electrical parts in the vertical rib type support frame 533 are located at the same plane, the holes 5331 for fixing the second positioning pieces may be counterbores, such that an end of the second positioning piece away from the rotating axis M is sunken in the corresponding hole 5331 to avoid the second positioning piece beyond the vertical rib type support frame 533 to damage the mounted electrical parts. When the second positioning piece is a screw, nut of the screw may be sunken in the corresponding hole 5331 and threaded tip of the screw may extend into the rotating base 510, thereby achieving connection between the vertical rib type support frame 533 and the rotating base 510.

The width of the vertical rib type support frame 533 refers to a length in the circumferential direction of the rotating base 510, and the height thereof refers to a length in the radial direction of the rotating base 510.

As shown in FIG. 5, the load-carrying part 530 may include an even number of the vertical rib type support frame 533. The vertical rib type support frame 533 may be disposed pairwise. In other words, the vertical rib type support frame 533 can be used in pairs. In this way, mounting relatively large weight of box type electrical parts may be more convenient.

The first positioning pieces and the second positioning pieces may be screws, and also may be removable connectors, such as pins.

As shown in FIG. 5, the vertical rib type support frame 533 may also be connected with the flat plate type support frame 532. For example, the load-carrying part 530 may further include an L-shaped connecting block 534. One edge of the connecting block 534 is connected with the flat plate type support frame 532, and the other edge of the connecting block 534 is connected with the vertical rib type support frame 533. In this case, the flat plate type support frame 532 and the vertical rib type support frame 533 both include mounting holes for matching the connecting block 534, such as holes 5333 in the vertical rib type support frame, as shown in FIG. 8.

When the flat plate type support frame 532 is connected with the vertical rib type support frame 533, an axial end of the flat plate type support frame 532 may be connected with the reinforcement 520 through holes 5323, while the vertical rib type support frame 533 is not connected with the reinforcement 520. In this way, the vertical rib type support frame 533 may be associated with the reinforcement 520 by the flat plate type support frame 532, thereby effectively balancing stability and mounting convenience.

In an example, the rotating base 510 may further include a flat plate type support frame mounting plane 515 and a vertical rib type support frame mounting plane 516 to facilitate mounting the flat plate type support frame 532 and the vertical rib type support frame 533. The flat plate type support frame mounting plane 515 and the vertical rib type support frame mounting plane 516 may not be located at the same plane, for example, they can be set close to each other at a particular inclined angle.

Combined with FIG. 6, different mounting planes on the rotating base 510 may all be provided with holes for fixture, where the axis of the respective holes for fixing the flat plate type support frame 532 and the axis of the respective holes for fixing the vertical rib type support frame 533 are all perpendicular to the rotating axis M. In an example, the rotating base 510 may be made of aluminum alloy to reduce weight, driving force and the centrifugal force.

The present disclosure further provides a CT machine with the above-described rotator. For the CT machine in the present disclosure, descriptions are made only to the rotator, and details of other parts may be seen in previous examples, and further description is omitted for brevity.

The above are detailed descriptions of the CT machine and the rotator thereof provided in the present disclosure. Specific examples are utilized herein to set forth the principles and implementations of the present disclosure, and the descriptions of the above examples are merely meant to help understanding the core ideas of the present disclosure. It should be noted that a plurality of improvements and modifications can also be made to the present disclosure by those of ordinary skill in the art without departing from the principles of the present disclosure, and such improvements and modifications shall all fall into the scope of protection of the claims of the present disclosure.

The invention claimed is:

1. A rotator of a Computed Tomography (CT) machine, comprising:
   a rotating base with a scanning hole;
   a reinforcement with an axial through hole, wherein the reinforcement is located at an axial end of the rotating base, and wherein the reinforcement is of a circumferentially closed structure and the axial through hole communicates with the scanning hole in a way that the reinforcement does not axially block the scanning hole; and
   a load-carrying part for carrying scanning parts, wherein the load-carrying part is mounted on an external peripheral surface of the rotating base and an axial end of the load-carrying part is connected with the reinforcement, and the load-carrying part is plate-shaped.

2. The rotator of claim 1, wherein,
   the reinforcement comprises a plurality of pulling plates; and
   each of the pulling plates of the plurality of pulling plates is circumferentially connected in sequence to form the circumferentially closed structure.

3. The rotator of claim 2, wherein,
   the scanning parts comprise a detector for receiving a ray beam;
   the reinforcement comprises a first pulling plate of the plurality of pulling plates which is of arc-shape and matches the detector; and a detector mounting plane is provided on the rotating base in a way that the detector mounting plane and the first pulling plate form a cavity for mounting the detector.

4. The rotator of claim 3, wherein the reinforcement further comprises a second pulling plate, a third pulling plate, and a fourth pulling plate of the plurality of pulling plates; wherein,
the second pulling plate and the third pulling plate both extend from top to bottom;
respective lower ends of the second pulling plate and the third pulling plate are connected with two ends of the first pulling plate, respectively; and
respective upper ends of the second pulling plate and the third pulling plate are connected by the fourth pulling plate.

5. The rotator of claim 4, wherein the second pulling plate, the third pulling plate, and the fourth pulling plate are all straight plates.

6. The rotator of claim 4, wherein the reinforcement is symmetrical relative to a line connecting midpoints of the first pulling plate and the fourth pulling plate.

7. The rotator of claim 4, wherein,
the scanning parts further comprise a tube for emitting the ray beam; and
the load-carrying part further comprises a ray box for mounting the tube, wherein an axial end of the ray box is connected with the fourth pulling plate.

8. The rotator of claim 1, wherein,
the load-carrying part comprises a flat plate type support frame;
the rotator further comprises one or more first positioning pieces perpendicular to a rotating axis of the rotator, wherein the one or more first positioning pieces include screws or pins; and
a plate surface of the flat plate type support frame fits the external peripheral surface of the rotating base and is connected with the rotating base by the one or more first positioning pieces.

9. The rotator of claim 8, wherein,
the load-carrying part further comprises a vertical rib type support frame;
the rotator further comprises one or more second positioning pieces perpendicular to the rotating axis of the rotator; and
a plate surface of the vertical rib type support frame is not parallel to the plate surface of the flat plate type support frame and is connected with the rotating base by the one or more second positioning pieces.

10. The rotator of claim 9, wherein,
the vertical rib type support frame further comprises a counterbore provided on a side away from the rotating axis of the rotator; and
the counterbore is configured to prevent the one or more second positioning pieces from extending out of the side.

11. The rotator of claim 9, wherein,
the flat plate type support frame and the vertical rib type support frame are connected with each other by an L-shaped connecting block;
an axial end of the flat plate type support frame is connected with the reinforcement; and
the vertical rib type support frame is connected to the reinforcement through the flat plate type support frame.

12. The rotator of claim 9, wherein an even number of the vertical rib type support frames are disposed pairwise.

13. A Computed Tomography (CT) machine, comprising:
a scanning bed system for carrying a subject; and
a rotator, wherein the rotator comprises:
a rotating base with a scanning hole;
a reinforcement with an axial through hole, wherein the reinforcement is located at an axial end of the rotating base, and wherein the reinforcement is of a circumferentially closed structure and the axial through hole communicates with the scanning hole in a way that the reinforcement does not axially block the scanning hole; and
a load-carrying part for carrying scanning parts, wherein the load-carrying part is mounted on an external peripheral surface of the rotating base and an axial end of the load-carrying part is connected with the reinforcement, and the load-carrying part is plate-shaped.

14. The CT machine of claim 13, wherein,
the reinforcement comprises a plurality of pulling plates; and
all the pulling plates are circumferentially connected in sequence to form the circumferentially closed structure.

15. The CT machine of claim 14, wherein,
the scanning parts comprise a detector for receiving a ray beam;
the reinforcement comprises a first pulling plate of the plurality of pulling plates which is of arc-shape and matches the detector; and
a detector mounting plane is provided on the rotating base in a way that the detector mounting plane and the first pulling plate form a cavity for mounting the detector.

16. The CT machine of claim 15, wherein the reinforcement further comprises a second pulling plate, a third pulling plate, and a fourth pulling plate of the plurality of pulling plates; wherein,
the second pulling plate and the third pulling plate both extend from top to bottom;
respective lower ends of the second pulling plate and the third pulling plate are connected with two ends of the first pulling plate, respectively; and
respective upper ends of the second pulling plate and the third pulling plate are connected by the fourth pulling plate.

17. The CT machine of claim 13, wherein,
the load-carrying part comprises a flat plate type support frame;
the rotator further comprises one or more first positioning pieces perpendicular to a rotating axis of the rotator, wherein the one or more first positioning pieces include screws or pins; and
a plate surface of the flat plate type support frame fits the external peripheral surface of the rotating base and is connected with the rotating base by the one or more first positioning pieces.

18. The CT machine of claim 17, wherein,
the load-carrying part further comprises a vertical rib type support frame;
a plate surface of the vertical rib type support frame is not parallel to the plate surface of the flat plate type support frame and is connected with the rotating base by one or more second positioning pieces perpendicular to the rotating axis of the rotator.

19. The CT machine of claim 18, wherein,
the vertical rib type support frame further comprises a counterbore provided on a side away from the rotating axis of the rotator; and
the counterbore is configured to prevent the one or more second positioning pieces from extending out of the side.

20. The CT machine of claim 18, wherein,
the flat plate type support frame and the vertical rib type support frame are connected with each other by an L-shaped connecting block;
an axial end of the flat plate type support frame is connected with the reinforcement; and
the vertical rib type support frame is connected to the reinforcement through the flat plate type support frame.

\* \* \* \* \*